United States Patent [19]

Masse et al.

[11] 4,378,698
[45] Apr. 5, 1983

[54] AMPLITUDE AND PHASE DETECTOR IN A HARMONIC OSCILLATOR SYSTEM

[75] Inventors: Lucien Masse; William L. Medlin, both of Dallas; James H. Sexton, Duncanville, all of Tex.

[73] Assignee: Mobil Oil Corporation, New York, N.Y.

[21] Appl. No.: 259,770

[22] Filed: May 1, 1981

[51] Int. Cl.³ .............................................. G01N 29/00
[52] U.S. Cl. ......................................... 73/579; 73/594
[58] Field of Search ................. 73/579, 581, 594, 662, 73/668, 778

[56] References Cited

U.S. PATENT DOCUMENTS 4,170,141 10/1979 Woo ....................................... 73/579
4,297,884 11/1981 Leveque et al. ....................... 73/579

Primary Examiner—Howard A. Birmiel
Attorney, Agent, or Firm—Charles A. Huggett; Michael G. Gilman; George W. Hager

[57] ABSTRACT

A harmonic oscillator and motion detection system for use in measuring dynamic elastic constants of rock material samples includes a pair of masses vertically suspended from a support position by a pair of wires. At least one mass is driven by a permanent magnet with the driving coil positioned in the air gap to the magnet. The rock sample is horizontally positioned between the pair of masses such that the rock sample acts as a spring element connecting the masses, thereby forming the simple harmonic oscillator. The motion detection system includes a pair of coil-magnets mounted to each mass for use in determining the amplitude and phase of the motion of the pair of masses.

4 Claims, 5 Drawing Figures

NORMALIZED DRIVING CURRENT I VS. FREQUENCY IN A BEREA SAMPLE

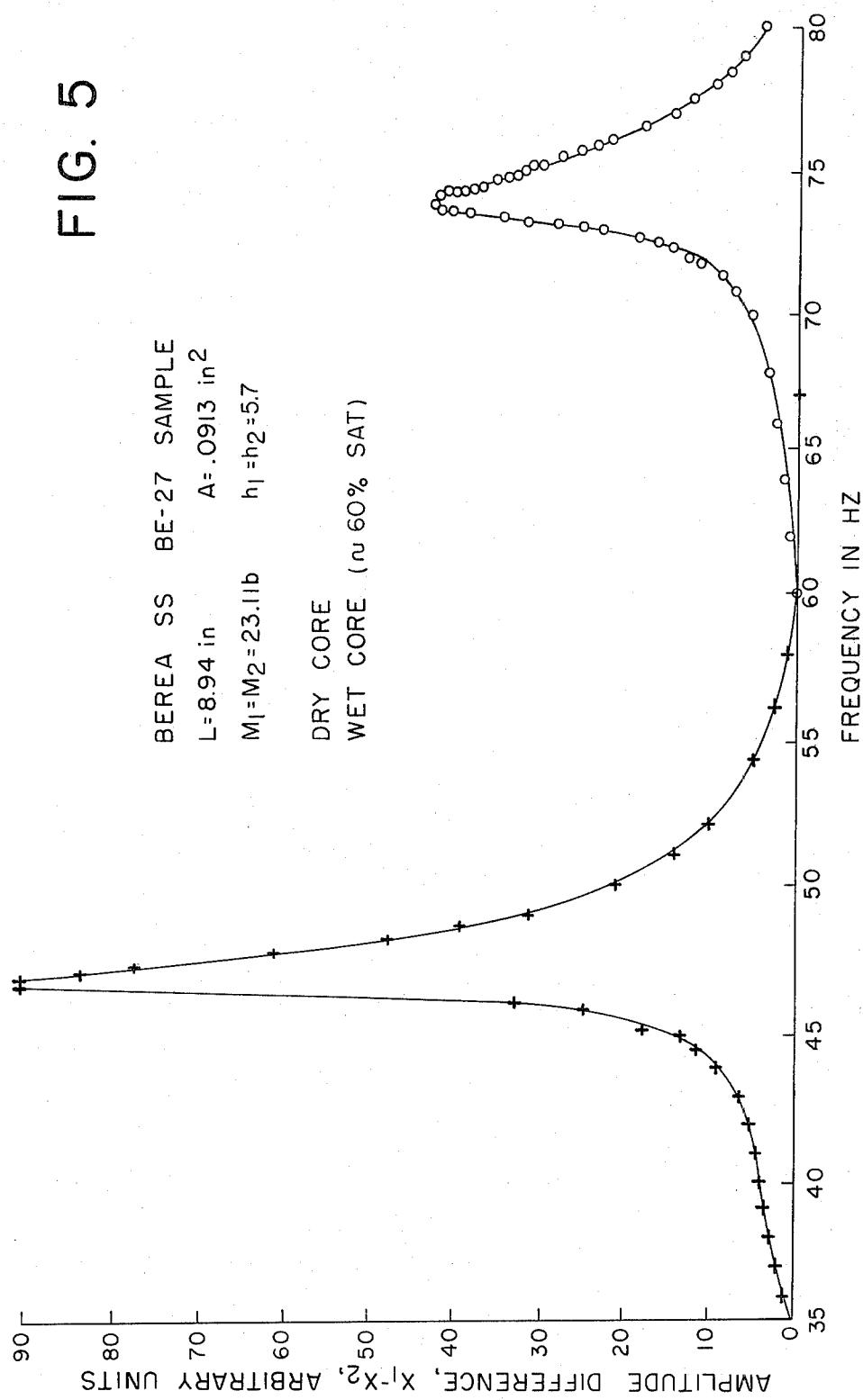

AMPLITUDE AND PHASE DETECTOR IN A HARMONIC OSCILLATOR SYSTEM

BACKGROUND OF THE INVENTION

Many seismic investigation techniques have been developed. For the most part these investigations have been guided by three main sources of data: field seismic records, well logs, and laboratory measurements of ultrasonic pulse velocities in core samples of rock materials. With respect to ultrasonic pulse velocity measurements the travel time of an ultrasonic wavelet is measured between ends of a cylindrical or prismatic bar of rock material. Experimental techniques require a signal wavelet which has died out at the excitation end before it is detected at the receiving end. For samples of practical length this requires a signal frequency of the order of hundreds of kHz. Seismic data are limited to frequencies below a few hundred hertz. Consequently the ultrasonic pulse velocity technique has not permitted measurements at frequencies approaching the seismic range.

SUMMARY OF THE INVENTION

In accordance with the present invention, there is disclosed a harmonic oscillator and motion detection system for use with rock materials in the seismic frequency range.

More particularly, a harmonic oscillator includes a pair of masses vertically suspended from a support position by a pair of thin wires. At least one of such masses is driven by a permanent magnet with driving coil positioned within its air gap. A sinusoidal driving current is applied to such coil for applying the driving force through interaction with the field of the magnet which is attached to the mass. A rock material sample is clamped horizontally between the pair of masses and acts as the spring element of a simple spring-mass harmonic oscillator system. A pair of motion detectors is attached to each of the masses. These detectors consist of a pair of small permanent magnets with coils positioned within their air gaps. Motion of the masses produces an emf signal in the coils which, for sinusoidal motion of the masses, is proportional to the derivative of the amplitude of the masses at any instant. A detector system measures the components of the coil detector emf which are in phase and in quadrature with the driving current.

BRIEF DESCRIPTION OF THE DRAWINGS

FIGS. 4 & 5 show resonance measurements carried out by the harmonic oscillator and motion detection system of FIGS. 1-3.

DESCRIPTION OF THE PREFERRED EMBODIMENT

The present invention relates to a system for measuring amplitude and phase of the motion in samples of rock material driven at seismic frequencies in a harmonic oscillator system which can be used to determine wave velocities and attenuation coefficients.

Figure 1:
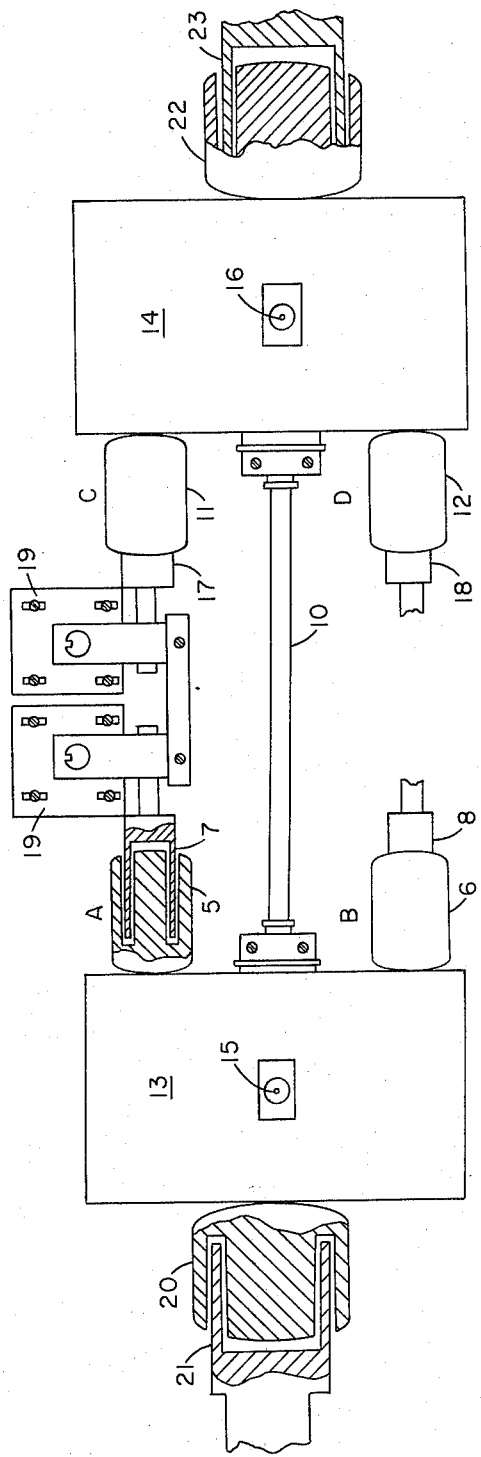
FIGS. 1-3 illustrate the harmonic oscillator and motion detection system of the present invention.

Referring now to FIG. 1 there will first be described the mechanical harmonic oscillator with which the amplitude and phase detection system of the present invention is utilized. Such oscillator uses the concept of a mass-spring system with a rock sample acting as the spring. Resonant frequency is determined not only by the dimensions of the rock, which control the spring constant, but by the mass, which can be made very large. By using a large enough mass, resonant frequencies in the seismic range are produced with rock samples from 6 to 10 inches in length. From the resonant frequency the spring constant and Young's modulus of the rock can be determined. An advantage of this method is that it is not necessary to make measurements far below the resonant frequency or to use samples of impractical dimensions to operate in the seismic frequency range. The spring-mass system can also be constructed so as to keep parasitic damping negligibly low. Since the dynamic properties of many rock materials, are amplitude sensitive, it is important that the amplitude of oscillation be kept at or near seismic levels which is possible by this method.

The rock sample 10 is clamped in a horizontal position between the two masses 13 and 14 which are suspended from a fixed support (not shown) by means of the wires 15 and 16 respectively. For the best results the support is seismically isolated from the earth. Mass 13 is attached to a permanent magnet 20 while mass 14 is attached to a permanent magnet 22. Driving coils 21 and 23 are positioned in the air gaps of the magnets 20 and 22, respectively to provide a conventional means for current applying driving forces to the masses 13 and 14. A sinusoidal current of frequency f is applied to each coil with the appropriate polarity to drive the masses in opposition.

The system has two natural modes of vibration, a high frequency one in which the two masses, 13 and 14, move in opposite directions and a lower frequency one in which they move in the same direction. Longitudinal oscillations are produced in the rock sample 10 when the masses move in opposition. This condition is provided when the system is symmetrical, that is, when the masses 13 and 14 are equal, the lengths of wires 15 and 16 are equal, the driving currents to the coils 21 and 22 are equal, and the magnetic field strengths in the air gaps of the magnets are equal. Under such conditions, the low frequency mode is largely eliminated and there is a single prominent resonance. The resonant frequency with no damping, $f_o$, is given by $$f_o = \frac{1}{2\pi} \sqrt{\frac{g}{h} + \frac{2K}{M}} \qquad (1)$$

where g is acceleration due to gravity, M is mass, h is wire length, and K is the spring constant of the rock. With damping, the resonant frequency, $f_m$, is given by $$f_m = f_o \sqrt{1 - 2\epsilon^2} \qquad (2)$$

where $\epsilon$ is a damping coefficient given by $\frac{1}{4}\pi$ times the fractional energy loss per cycle of oscillation. In practice $g/h < < 2K/M$ and if damping is small, $2\epsilon^2 < < 1$. Then $$f_m \approx \frac{1}{2\pi} \sqrt{\frac{2K}{M}} \qquad (3)$$

If the rock is treated as an elastic material, K is related to Young's modulus through the equation $$K = (EA/L) \qquad (4)$$

where A is cross-sectional area and L is length of the rock sample. The bar velocity V in a cylindrical core or prismatic bar of material with modulus E is given by $$V = \sqrt{E/\rho} = \pi f_m \sqrt{\frac{2ML}{A\rho}} \quad (5)$$

where $\rho$ is density of the material.

To the extent that a given rock material is perfectly elastic in behavior, and the system of FIG. 1 is free of damping, equation (5) can be used to determine a bar velocity from measurement of resonant frequency $f_m$. The bar velocity is the velocity a seismic wave would have in a thin prismatic bar such as the rock sample of FIG. 1. The velocity of a seismic wave in the earth is related to bar velocity as follows:

$$V_{earth} = V\sqrt{(1-\nu)/(1+\nu)(1-2\nu)} \quad (6)$$

where $\nu$ is the Poisson Ratio of the rock sample material.

To account for departures from elastic behavior of the rock and damping due to pore fluids a more refined analysis can be used. The damping coefficient $\epsilon$ can be determined from analysis of displacement amplitude vs. frequency data and from measurements of phase shift between driving signal and displacement. Viscoelastic constants which account for pore fluid behavior can be derived from this analysis and used to calculate velocity attenuation and reflection coefficient at interfaces. Results obtained in this way take account of the influence of pore fluids in the rock sample.

The frequency range of investigation depends on masses 13 and 14, on E for the rock material 10 and on sample dimensions. For a cylindrical rock sample 10 with E of $10^6$ psi, core diameter of 0.30 inches, wire length of 8 inches, and masses of 20 lbs. each, the resonant frequency $f_m$ is about 93 hertz. Higher frequencies can be investigated by decreasing masses 13 and 14, decreasing rock sample 10 in length or increasing rock sample 10 in diameter. Lower frequencies can be obtained by making changes in the opposite sense.

Figure 2:
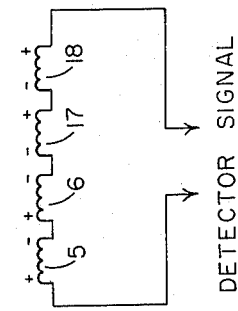

Measurement of $f_m$ requires a method for measuring the motion or displacements $X_1$ and $X_2$ of the masses 13 and 14, respectively, or their difference. It is, therefore, a specific feature of the present invention to provide a method for measuring the relative motion or displacement $|X_1 - X_2|$ of such masses. A pair of identical permanent magnets 5 and 6 are attached to the mass 13 and a pair of identical permanent magnets 11 and 12 are attached to the mass 14 with their axes lying in a plane perpendicular to the plane of the wire supports, 15 and 16. Identical coils 7, 8, 17 and 18 are positioned in the air gaps of each of the magnets 5, 6, 11 and 12 respectively. These coils are rigidly mounted on the oscillator frame through alignment brackets, 19. Motion of the masses produces an emf in the detector coils. By connecting the coils in series with appropriate polarity as shown in FIG. 2, the signals due to motion of the masses in opposition add and give an emf proportional to $|X_1 - X_2|$.

The geometry of the coil-magnet detectors used here is very effective in reducing noise due to wobble of the masses. Wobble, which produces lateral motion of the masses, does not induce significant emf in the detector coils. Wobble associated with motion of the masses in the same direction is highly damped and therefore not significant. Wobble associated with rotation of the masses about their wire supports produces flexure of the rock sample and is the dominant noise signal in the measurements. It is therefore a specific feature of the present invention to provide a detection system which reduces this noise signal to a very low level. More particularly, rotational motion of the masses causes detector magnets 5 and 11 to move towards one another while detector magnets 6 and 12 move away from one another. Consequently, the series connection of magnet coils 7 and 8 in opposition to coils 17 and 18, as illustrated in FIG. 2, produces emf signals of opposite polarity which tend to cancel thereby reducing the noise signal.

Figure 3:
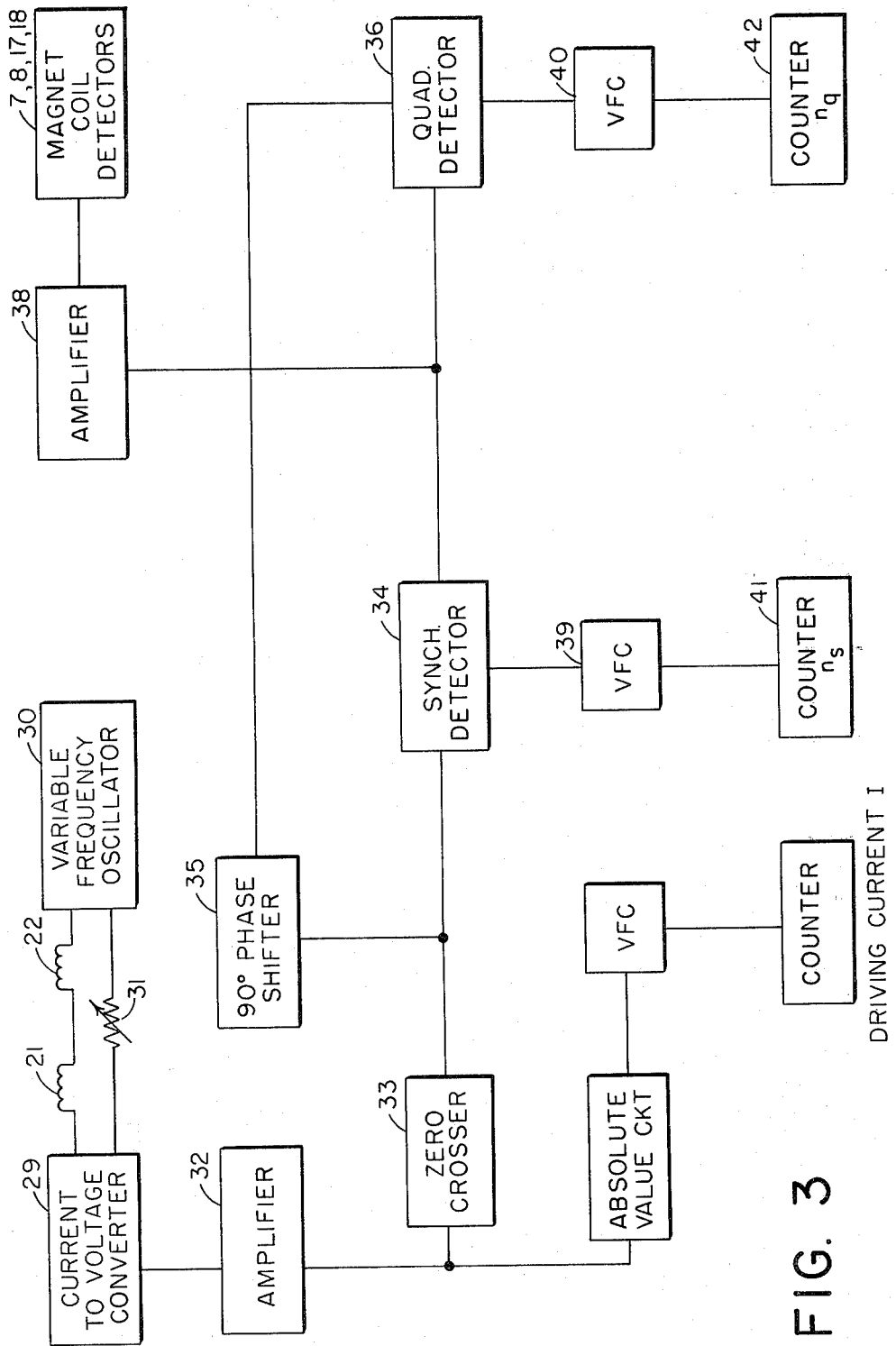

Referring now to FIG. 3, there is illustrated the circuitry for converting the coil displacements into amplitude and phase representations. A variable frequency oscillator 30 provides the sinusoidal driving current to the driving coils 21 and 23. These coils are connected in series with appropriate polarity to drive the masses in opposition. A voltage developed across a resistor 31 with negligible reactance and wired in series with the coils has the same phase as the driving current. This voltage is applied through current-to-voltage converter 29 and amplifier 32 to a zero crosser circuit 33. The output of the zero crosser circuit 33 is a square wave signal in phase with the driving current. This square wave signal is applied to an in-phase detector 34 and a 90° phase shifter 35. The 90° lagging square wave from shifter 35 is applied to a quadrature detector 36. Also applied to both detectors 34 and 36 is the amplified signals from the coil-magnet displacement detectors 37.

The in-phase detector 34 and quadrature detector 36 function to detect only signals which are in phase or coherent with their square wave input signals. The in-phase detector 34 passes only that part of the detector coil voltage which is in phase with the driving current. The quadrature detector passes only that part of the detector coil voltage which is 90° out of phase with the driving current.

The outputs of detectors 34 and 36 are applied to voltage-to-frequency converters 39 and 40 respectively. Each converter generates pulses whose frequency is proportional to the average value of the rectified peak voltage passed by the detectors. If the detector voltage is amplified by a factor G, then the average value of the synchronous voltage produced by the detector 34 is:

$$e_s = \frac{1}{T_0} \int^T Ge_m\cos(\omega t + \phi)dt = k_s n_s + b_s \quad (7)$$

and the quadrature voltage produced by the detector 36 is:

$$e_q = \frac{1}{T_0} \int^T Ge_m\sin(\omega t + \phi)dt = k_g n_g + b_g \quad (8)$$

where:
$e_m$ = emf of mass
$\phi$ = phase angle between driving current and displacement
$n_s$ and $n_g$ = counting rates at each counter 41 and 42
$k_s$ and $k_g$ = proportionality constants
$\omega = 2\pi f$
$b_s$ and $b_g$ = intercepts determined by bias conditions of converters 39 and 40

T = period of the driving current

Amplitude $X_m$ and phase motion $\phi$ of the masses can be determined from the following expression:

$$X_m = V/GSf, \text{ and} \tag{9}$$

$$\phi = \tan^{-1}[(k_g n_g + b_g)/(k_s n_s + b_s)] \tag{10}$$

where:
V = synchronous voltage
S = detector sensitivity
f = frequency

In the preferred embodiment, such amplitude and phase was determined through use of a Data General Nova series minicomputer used in conjunction with the detection system of the present invention.

Using the motion/detector system of the present invention the resonant frequency $f_m$ can be determined by plotting the coil emf against frequency f of the driving current. FIG. 5 shows resonance measurements made for a Berea sandstone sample in the harmonic oscillator of FIG. 1. Dimensions of the cylindrical rock sample were a diameter of 0.341 inches and a length of 8.94 inches. Masses 13 and 14 were 23.1 lb each and the lengths of wires 15 and 16 were 5.7 inches. Results are shown for the sample in a dry state and in a wet state where saturation conditions were about 60% water and 40% gas. The dry state resonance frequency of 73.9 Hz corresponds to a Young's modulus of $0.65 \times 10^6$ psi and V = 4800 ft/sec. The wet state value resonance frequency of 46.5 hz. corresponds to a Young's modulus of $0.26 \times 10^6$ psi and V = 3020 ft/sec.

Figure 4:
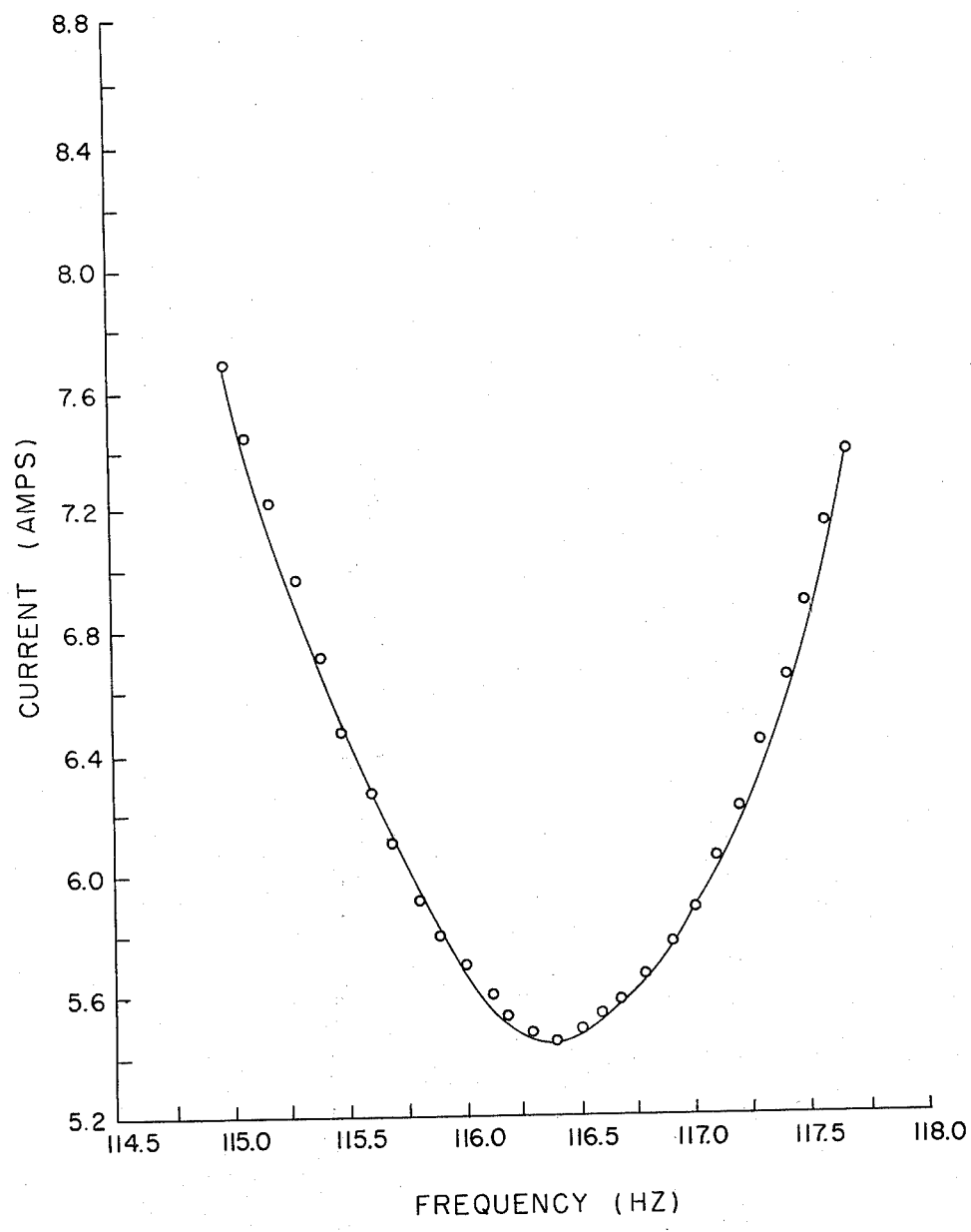

Most rock materials show significant non-linear resonance behavior. Near resonance the amplitude of oscillations changes with time and depends on how resonance is approached. The resonance peak itself does not fit the classical equations for a simple harmonic oscillator very well. These problems can be avoided by making the resonance measurements at constant amplitude. This can be done by means for adjusting the driving current at each frequency to obtain a preselected amplitude $|X_1 - X_2|$ such as 500 Angstroms. A plot of driving current vs. frequency then replaces the amplitude plot of FIG. 5. A typical measurement of this type is shown in FIG. 4. The resonance curve is inverted in this case with frequency corresponding to a minimum current rather than a maximum amplitude. However, the equations for a simple harmonic oscillator still apply to the driving current curve in a conventional way.

Constant amplitude measurements made in this way fit the classical harmonic oscillator equations very closely. Therefore the shape of the resonance peak can be used to measure damping of seismic frequency waves through the loss factor $Q_E = \frac{1}{2}\epsilon$. The Q associated with longitudinal oscillations is called $Q_E$, the extensional loss factor, and is given by $$Q_E = f_m/(f_2 - f_1) \tag{11}$$

where $f_1$ and $f_2$ are the frequencies at which the driving current is $\sqrt{2}$ times the current at the resonant frequency $f_m$. If a quadrature detector or other system is used which provides phase data, $f_1$ and $f_2$ are the frequencies at which the phase angle $\phi$ between displacement and driving current is 135° and 225°, respectively, where $\phi$ is taken to be 180° at $f = f_m$.

In the foregoing described embodiment of the invention, the harmonic oscillator of FIG. 1 has been described as a symmetric system with the masses 13 and 14 being driven in opposition by the means of the magnets 11 and 12 and driving coils 17 and 18. However, the system need not be symmetric to obtain useful results. Mass 13 can be different from mass 14 and one of the magnet-driving coil combinations can be removed. In such a non-symmetric system, the mass M in equations 1, 3 and 5 above may be replaced by the expression $$M = 2M_1 M_2/(M_1 + M_2). \tag{12}$$

While a particular embodiment of the invention has been shown and described, additional modifications are within the spirit and scope of the invention. The appended claims are intended to cover all such modifications.

What is claimed is:

1. In a system for measuring dynamic elastic constants of rock materials having a rock material horizontally supported between a pair of masses which are vertically suspended and a coil-magnet system driven by a sinusoidal current such that the masses move in opposition with the rock material acting as a spring element connecting them, the improvement comprising:
    (a) a pair of coil-magnet displacement detectors mounted on each of said masses,
    (b) means for connecting the coils of said coil-magnet displacement detectors so as to produce an emf displacement signal across said coils that is proportional to the relative displacements of said masses,
    (c) a resistive element connected in series with the driving coils to said masses, whereby the voltage across said resistive element has the same phase as said sinusoidal driving current,
    (d) means for utilizing the voltage across said resistive element to produce a first square wave signal in phase with the driving current and a second square wave signal 90° out of phase with said first square wave signal,
    (e) a synchronous detector to which said displacement signal and said first square wave signal are applied, said detector producing a output when said displacement signal is in phase with said first square wave signal,
    (f) a quadrature detector to which said displacement signal and said second square wave signal are applied, said detector producing a signal when said displacement signal is in phase with said second square wave signal.

2. The system of claim 1 further including means for converting the signals from said synchronous and quadrature detectors into a representation of the amplitude and phase motion of said masses.

3. The system of claim 1 wherein a first of said displacement detectors on each of said masses are located such that they move towards one another as the masses rotate about their vertical support and the second of said displacement detectors on each of said masses are located such that they move away from one another as the masses rotate about their vertical support.

4. The system of claim 3 wherein the magnet coils of said displacement detectors are connected in series such that the emf's of the pair of magnet coils located on one of said masses are in polarity opposition to the emf's of the pair of magnet coils located on the other of said masses.

* * * * *